United States Patent [19]

Bilgrien et al.

[11] Patent Number: 5,017,671

[45] Date of Patent: May 21, 1991

[54] POLYCYCLOSILOXANES CONTAINING SILACYCLOBUTANE

[75] Inventors: Carl J. Bilgrien; Chi-long Lee, both of Midland, Mich.

[73] Assignee: Dow Corning Corporation, Midland, Mich.

[21] Appl. No.: 422,209

[22] Filed: Oct. 16, 1989

[51] Int. Cl.$^5$ ............................................. C08G 77/06
[52] U.S. Cl. ........................................ 528/21; 528/37; 528/40; 556/450
[58] Field of Search ............................ 528/40, 21, 37; 556/450

[56] References Cited

U.S. PATENT DOCUMENTS 3,046,291  7/1962  Sommer ........................... 260/448.2
3,719,696  3/1973  Jonas et al. ........................... 528/37

Primary Examiner—Melvyn I. Marquis
Attorney, Agent, or Firm—Edward C. Elliott

[57] ABSTRACT

This invention describes a polycyclosiloxane of the formula

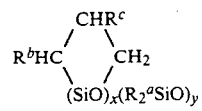

where $R^a$, $R^b$, and $R^c$ are independently monovalent radicals; x is an integer equal to or greater than 3, y is equal to or greater than 0, and x plus y is greater than 3. A process for the production of the polycyclosiloxane above consisting essentially of (A) adding a solvent solution of 1,1-dichlorosilacyclobutane, and optionally dichlorodiorganosilane, to a mixture of water and solvent with rapid stirring at room temperature at a rate which does not cause the mixture to raise in temperature, (B) washing with water, (C) drying with MgSO$_4$, (D) filtering, and (E) removing the solvent. Methods of using the polycyclosiloxane of silacyclobutane as an ingredient in a silicone composition which cures on exposure to moisture to give an elastomer is claimed, as is the composition produced.

17 Claims, No Drawings

POLYCYCLOSILOXANES CONTAINING SILACYCLOBUTANE

BACKGROUND OF THE INVENTION

1. Field of the Invention

This invention relates to polycyclosiloxanes containing silacyclobutane and their use.

2. Background Information

The preparation of silacyclobutanes of the formula

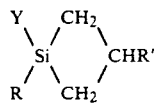

where Y is chlorine or hydrogen, R' is hydrogen or methyl, and R is a monovalent hydrocarbon radical free of aliphatic unsaturation, and polymers derived therefrom, were revealed by Sommer in U.S. Pat. No. 3,046,291, issued July 24, 1962. Polymerization was accomplished upon heating or simply standing and optionally in the presence of a catalyst from the group consisting of alkaline materials such as NaOH, KOH LiOH; quaternary ammonium compounds; and metallic salts of sodium, aluminum, iron, cobalt, manganese, lead and zinc.

SUMMARY OF THE INVENTION

Cyclic siloxanes of silacyclobutane are obtained by the slow hydrolysis of 1,1-dichlorosilacyclobutane under acidic conditions. An admixture of the cyclic siloxane of silacyclobutane, silanol terminated polydiorganosiloxane, and a catalytic amount of a nucleophilic base gives a composition which is stable in the absence of moisture, but which cures to an elastomer upon exposure to moisture. A composition which is stored as two parts comprises a first part comprising a portion of a silanol terminated polYdiorganosiloxane and a copolymer of a cyclic siloxane of silacyclobutane and a diorganocyclosiloxane and a second part comprising the remainder of the silanol terminated polydiorganosiloxane and a catalytic amount of a nucleophilic base. When the two parts are combined curing begins immediately, but further crosslinking reaction takes place upon exposure to moisture, to give an elastomer.

DESCRIPTION OF THE INVENTION

This invention relates to a polycyclosiloxane of the formula

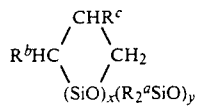

where $R^a$, $R^b$, and $R^c$ are independently monovalent radical selected from the group consisting of hydrogen atom, hydrocarbon, or substituted hydrocarbon; x is an integer equal to or greater than 3, y is equal to or greater than 0, and x plus y is greater than 3; and a process for the production of the polycyclosiloxane above consisting essentially of (A) adding a solvent solution og 1,1-dichlorosilacyclobutane, and optionally dichlorodiorganosilane, to a mixture of water and solvent with rapid stirring at room temperature at a rate which does not cause the mixture to raise in temperature, (B) washing with water, (C) drYing with dessicant, such as MgSO$_4$, (D) filtering, and (E) removing the solvent. When y is zero, the silacyclobutane functional polycyclosiloxane can be used as an ingredient in a silicone composition which cures on exposure to moisture to give an elastomer comprising (A) 100 parts by weight of a silanol functional polydiorganosiloxane, (B) from 0.1 to 100 parts by weight of the silacyclobutane functional polycyclosiloxane and (C) from 0.01 to 1.0 part by weight of nucleophilic base. When y is greater than 0, the silacyclobutane functional polycyclosiloxane can be used as an ingredient in a silicone composition which cures on exposure to moisture to give an elastomer comPrising (B) 100 parts by weight of the silacyclobutane functional polycyclosiloxane and (C) from 0.01 to 1.0 part by weight of nucleophilic base. A silicone composition which is stored in 2 Parts and which cures to give an elastomer upon mixing the two parts comprises (A) 100 parts by weight of a silanol functional polydiorganosiloxane, (B) 0.1 to 100 parts by weight of the copolymer of a cyclic siloxane of silacyclobutane and a diorganocyclosiloxane obtained when y is greater than zero, and (C) from 0.01 to 1.0 parts by weight of nucleophilic base; part (C) being separated from the combination of part (A) and part (B) until the composition is to be used.

A method has been discovered for hydrolyzing 1,1-dichlorosilacyclobutane, and mixtures of 1,1-dichlorosilacyclobutane and dichlorodiorganosilane, to give siloxane cyclics of the formula

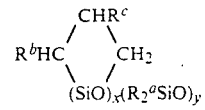

$R^a$, $R^b$, and $R^c$ are independently monovalent radical selected from the group consisting of hydrogen atom, hydrocarbon, or substituted hydrocarbon; x is an integer equal to or greater than 3, y is equal to or greater than 0, and x plus y is greater than 3. When y is 0, x is an integer of from 3 to 8, with a small proportion of higher molecular weight species present. The process gives a mixture of cyclic siloxanes as well as some high molecular weight material. The majority of the cyclics produced are tetracyclosiloxane and pentacyclosiloxane.

Exemplary of suitable monovalent radicals for the $R^a$, $R^b$, and $R^c$ groups are hydrogen, the hydrocarbons, or substituted hydrocarbons. Thus, for example, these groups can be alkyl such as methyl, ethyl, propyl, or octadecyl; substituted alkyl such as aminopropyl or thiopropyl; haloalkyl such as chloropropylary such as phenyl, xenyl, or naphthyl; alkaryl such as tolyl or xylyl; aralkyl such as benzyl; unsaturated alkenyl such as vinyl, propenyl, or hexenyl; and unsaturated alkynyl such as acetylenyl or propynyl. $R^a$ is preferably methyl. $R^b$, and $R^c$ are preferably methyl or hydrogen and most preferably hydrogen.

Several methods of preparing 1,1-dichlorosilacyclobutane are known in the art. A particularly useful method is the conventional Grignard reaction of 3-chloropropyltrichlorosilane and magnesium. It is preferred to use about an equimolar ratio of ingredients in the presence of an inert, anhydrous solvent, such as tetrhydrofuran. The preparation of dichlorodiorganosilane is well known in the art.

Conversion of the 1,1-dichlorosilacyclobutane, or mixture of 1,1-dichlorosilacyclobutane and dichlorodiorganosilane, to a cyclic siloxane is not obvious, as the conventional methods of producing cyclic siloxanes such as buffered hydrolysis or the use of ZnO result in intractable materials, and not the cyclic desired. The silacyclobutane ring is subject to attack by nucleophiles and electrophiles and also undergoes ring opening reactions with silanol. Successful preparation of the desired cyclic material requires complete intermolecular condensation of silanol groups and the absence of nucleophiles.

The generation of the desired cyclic siloxane of silacyclobutane is achieved by the slow addition of 1,1-dichlorosilacyclobutane into a rapidly stirred mixture of water and solvent, preferably ether. After the hydrolysis of the chlorine groups and subsequent condensation of the SiOH groups to give the cyclic material, the ether phase is washed to remove impurities, dried over a desiccant, filtered and stripped of solvent to give the desired cyclic material. The product is stable under the acid hydrolysis conditions, and the cyclic products are favored by use of a slow addition rate and a dilute solution.

Cyclic siloxane copolymers containing both silacyclobutane groups and diorganosiloxane groups can be produced by using a mixture of dichlorosilacyclobutane and dichlorodiorganosilane or diorganocyclosiloxane in the above process in place of the 1,1-dichlorosilacyclobutane alone.

Silacyclobutane functional polycyclosiloxane can be reacted with silanol functional polydiorganosiloxane in the presence of a catalytic amount of a nucleophilic catalyst such as N,N-diethylhydroxylamine to form an endblocked polymer through the ring opening of one of the silacyclobutane rings and then addition to the silanol. This can be illustrated as follows for the addition of an excess of tetracyclosiloxane of silacyclobutane with silanol terminated polydimethylsiloxane and a catalytic amount of N,N-diethylhydroxylamine:

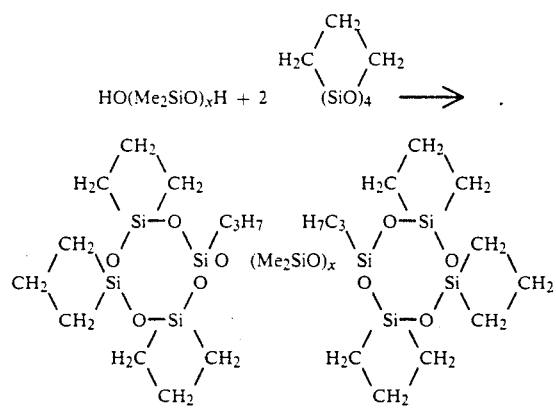

The Et$_2$NOH catalyst also adds to the silacyclobutane ring and thus some of the silacyclobutane rings in the above polymer may be expected to have the form:

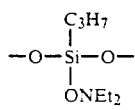

The formulations of silanol functional polydiorganosiloxane, silacyclobutane functional polycyclosiloxane, and catalytic amounts of diethylhydroxylamine were found to slowly gel with time, even in the absence of exposure to atmospheric moisture, with gel times of one day or more. Crosslinking is accelerated by exposure to moisture. When exposed to moisture, catalyzed hydrolysis of the silacyclobutane rings occurs, and subsequent condensation of the silanol groups which are formed leads to crosslinking of the polymer.

When cyclic siloxane copolymers of silacyclobutane and diorganosiloxane groups were formulated with silanol functional polydiorganosiloxane and a nucleophilic catalyst, the formulation gelled rapidly. Exposure to moisture caused the formulation to undergo more extensive crosslinking. This reactivity allowed the preparation of two-part formulations in which one part contained the cyclic siloxane copolymer of silacyclobutane and the other contained the nucleophilic catalyst. Following mixing of the parts, the product formed a nonflowing, nonslump material which cured completely upon exposure to atmospheric moisture. Suitable nucleophilic catalysts are the amines, hydroxyl amines, guanidine, N-alkylated guanidines, urea, and N-alkylated ureas.

The silanol functional polydiorganosiloxane used above is well known in the art. The organic group can be any monovalent hydrocarbon radical such as alkyl radicals such as methyl, ethyl, isopropyl, hexyl, or octadecyl; alkenyl radicals such as vinyl, allyl, or hexenyl; and aromatic hydrocarbon radical such as phenyl, tolyl or xylyl. The monovalent hydrocarbon radical can also be a halogenated hydrocarbon radical such as chloromethyl, 3,3,3-trichloropropyl, or radicals of the formula R$_f$CH$_2$CH$_2$—where R$_f$ can be any perfluoroalkyl groups such as trifluoromethyl.

The molar concentration of the polysiloxane of silacyclobutane is equal to or greater than the silanol concentration in order to prevent Premature crosslinking. A slight excess of the polysiloxane can be used to chain extend the polymer to give a more viscous polymer. Since the tetracyclosiloxane of silacyclobutane is a solid, it is advantageous to use a solvent to dissolve this polycyclosiloxane and disperse it throughout the polydiorganosiloxane. After the reaction is completed, the composition can be stripped of the solvent.

The silicone composition which cures upon exposure to moisture is particularly useful in the production of sealants because no metal catalyst is required. The nucleophilic catalyst that is used can be evaporated from the system following cure. The process does not generate any volatile byproducts such as acetic acid or alcohol that are found in some current silicone sealants.

Additional ingredients such as fillers and pigments can be added to the composition to reinforce and color the composition for use as a sealant in the same manner as is currently done for silicone sealants.

The following examples are included for illustrative purposes only and should not be construed as limiting the invention which is properly set forth in the appended claims.

EXAMPLE 1

A solution of 25.2 g of 1,1-dichlorosilacyclobutane in 79 g of ether was slowly added at room temperature to a rapidly stirred mixture of 50 ml of water and 22 g of ether over a 4.5 hour period. After stirring overnight, the ether phase was washed 3 times with 150 ml of water, dried over MgSO$_4$ for 30 minutes and filtered.

The ether was stripped away to yield a cloudy fluid. Analysis by infrared spectroscopy revealed little or no silanol present. A CHCl3 solution of the fluid was analyzed by gas chromatography and mass spectroscopy to disclose a distribution of cyclic siloxanes of silacyclobutane of the formula

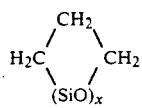

The material which eluted the gas chromatography apparatus showed a distribution as follows:

| x | percent present |
|---|---|
| 3 | 8.3 |
| 4 | 43.9 |
| 5 | 28.2 |
| 6 | 14.8 |
| 7 | 3.9 |
| 8 | 0.9 |
| | 100.0 |

An ether solution of the material was passed through a column of activated alumina and the recovery of the material was quantitative. From this it can be concluded that there was little or no silanol present. There was some higher molecular weight material to a number average molecular weight of 30,000.

The product exhibited no gelation over a time period of 7 days. After 24 hours the product had clarified to a crystalline solid in a clear colorless fluid. The crystals were shown to be the cyclic tetrasiloxane, having a melting temperature of 75° to 80° C. The crystals readily dissolved in toluene, chloroform and ether.

COMPARATIVE EXAMPLE 1

A buffered hydrolysis procedure such as is commonly used with polymerization of dichlorosilanes was tried unsuccessfully. A solution of 25.1 g of 1,1-dichlorosilacyclobutane in 57 g of ether was added rapidly (over a 17 minute period) to a rapidly stirred mixture of 102 g ether, 100 g water, and 50 g Et3N. After 30 minutes, the ether phase was washed 3 times with 150 ml of water, dried over MgSO4 for one hour, filtered and stripped of ether. After three days, the cloudy fluid product gelled to a friable rubbery solid.

COMPARATIVE EXAMPLE 2

Hydrolysis in the presence of ZnO such as is commonly used with dichlorosilanes was tried. A solution of 25 g of 1,1-dichlorosilacyclobutane in 50 g methyl acetate was added rapidly (12 minute period) to a stirred suspension of 21.3 g of ZnO in 100 g methyl acetate with generation of considerable exotherm. After stirring for 50 minutes, the mixture was filtered to give insoluble salts and a brittle rubber in the form of spaghetti strands. No siloxane products could be recovered from the filtered solvent.

EXAMPLE 2

A solution of 0.735 g of the hydrolysis product of example 1 and 2.21 g of ether was mixed with 2.01 g of hydroxyl endblocked polydimethylsiloxane having a $M_n$ (number average molecular weight) of 2,900 and a hydroxyl content of 1.18 percent by weight. To this solution was added 44 microliters of Et2NOH and the mixture was stripped of volatiles in a vacuum chamber. An 8 mil film drawn from this polymer on an aluminum panel was exposed to the atmosphere at 54 percent relative humidity to give a cured elastomer. The tack free time (time to lose the tacky surface) was 50 minutes. The unexposed composition remained fluid in the absence of moisture for greater than one week.

EXAMPLE 3

A solution of 0.169 g of the hydrolysis product of example 1 and 0.506 g of ether was mixed with 2.01 g of hydroxyl endblocked polydimethylsiloxane having a $M_n$ of 17,000 and a hydroxyl content of 0.2 percent by weight. To this solution was added 44 microliters of Et2NOH and the mixture was stripped of volatiles in a vacuum chamber. An 8 mil film drawn from this polymer on an aluminum panel was exposed to the atmosphere at 54 percent relative humidity to give a cured elastomer. The tack free time was 47 minutes. The unexposed composition remained fluid in the absence of moisture for a period of greater than 1 day.

EXAMPLE 4

A solution of 392 g of 1,1-dichlorosilacyclobutane, 117 g of dichlorodimethylsilane, and 310 ml of diethyl ether was slowly added at 0° C. to a rapidly stirring mixture of 400 ml water and 1000 ml diethyl ether. After the addition was completed, the ether phase was washed 3 times with 500 ml water, dried over MgSO4 and filtered. The solution was stripped to 37° C. 90 mm Hg to remove the ether solvent. The product of the formula

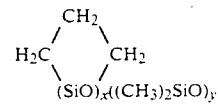

was analyzed by gas chromatography and showed the following distribution:

| | x = | | | | | |
|---|---|---|---|---|---|---|
| | 1 | 2 | 3 | 4 | 5 | 6 |
| y = | | | | | | |
| 0 | — | — | — | 4.4 | 4.5 | 1.4 |
| 1 | — | — | 20.1 | 16.4 | 4.5 | 1.0 |
| 2 | — | 11.0 | 12.5 | 4.6 | 1.7 | — |
| 3 | 1.5 | 2.9 | 1.6 | 0.6 | — | — |

This analysis shows that greater than 85 percent of the product contained at least three silacYclobutane rings per molecule.

EXAMPLE 5

A two part formulation was prepared mixed and cured. Part A consisted of 25 g of a silanol terminated polydimethylsiloxane of molecular weight ($M_n$) equal to 24,000 and 0.14% by weight hydroxyl groups (polymer X) and 0.72 g of the hydrolyzate product from Example 4. Part B consisted of 25 g polymer X and 0.25 g diethylhydroxyl amine. Parts A and B were loaded into separate chambers of a side-by-side extrusion tube and co-extruded through a 4 inch static mixing nozzle into a chase. The formulation gelled rapidly and was tack free in 7 minutes. The extruded formulation was further cured at room temperature and 50 percent relative humiditY. After 43 hours, an elastomer with the following properties had been formed: tensile, 44 psi; elongation, 389 percent; modulus at 100% elongation, 25 psi.

EXAMPLE 6

A two part formulation was prepared, mixed and cured. Part A consisted of 25 g of polymer X and 1.80 g of the hydrolyzate product from Example 4. Part B consisted of 25 g Polymer X and 0.25 g diethylhydroxyl amine. Parts A and B were loaded into seParate chambers of a side-by-side extrusion tube and co-extruded through a 4 inch static mixing nozzle into a chase. The formulation gelled rapidly and was tack free in 1 minute. The extruded formulation was further cured at room temperature and 50 percent relative humidity. After 43 hours, an elastomer with the following properties had been formed: tensile, 44 psi; elongation, 438 percent; modulus at 100% elongation, 18 psi.

EXAMPLE 7

A two part formulation was prepared, mixed and cured. Part A consisted of 25 g of polymer X and 0.72 g of the hydrolyzate product from Example 4. Part B consisted of 25 g polymer X and 0.063 g diethylhydroxyl amine. Parts A and B were loaded into separate chambers of a side-by-side extrusion tube and co-extruded through a 4 inch static mixing nozzle into a chase. The formulation gelled rapidly. The extruded formulation was further cured at room temperature and 50 percent relative humidity. After 43 hours, an elastomer with the following properties had been formed: tensile, 24 psi; elongation, 766 percent; modulus at 100% elongation, 12 psi.

EXAMPLE 8

A two part formulation was prepared, mixed and cured. Part A consisted of 25 g of polymer X and 1.80 g of the hydrolyzate product from Example 4. Part B consisted of 25 g polymer X and 0.063 g diethylhydroxyl amine. Parts A and B were loaded into separate chambers of a side-by-side extrusion tube and co-extruded through a 4 inch static mixing nozzle into a chase. The formulation gelled rapidly. The extruded formulation was further cured at room temperature and 50 percent relative humidity. After 43 hours, an elastomer with the following properties had been formed: tensile, 23 psi; elongation, 739 percent; modulus at 100% elongation, 10 Psi. The rise in viscosity upon extrusion was monitored separately by viscometer for the same formulation. The viscosities recorded were:

| | |
|---|---|
| initial (Part B only) | 14,400 cs |
| 1 minute after mixing | 104,000 |
| 2 minutes | 548,000 |
| 4 minutes | >8,000,000 (off scale) |

EXAMPLE 9

A two part formulation with fumed silica filler was prepared, mixed and cured. A base was prepared by mixing 26.6 g Cab-O-Sil MS-7 silica and 250 g of a silanol terminated polydimethylsiloxane with molecular weight ($M_n$) of 14,500 (0.23 percent hydroxyl radical on a weight basis) at high speed in a dental mixer for two minutes. a. Part A was formulated from 25 g of the base and 1.08 g of the hydrolyzate product of Example 4. Part B was formulated from 25 g of the base and 0.26 g diethylhydroxylamine. Parts A and B were co-extruded into a chase, tooled to form a slab and cured for 22 hrs at 50 percent relative humidity and 25° C. to give an elastomer with the following properties: tensile 220 psi; elongation, 354 percent; and modulus at 100% elongation, 76 psi. b. Part A was formulated from 25 g of the base and 2.69 g of the hydrolyzate product of Example 4. Part B was formulated from 25 g of the base and 0.26 g diethylhydroxylamine. Parts A and B were co-extruded into a chase, tooled to form a slab and cured for 22 hrs at 50 percent relative humidity and 25° C. to give an elastomer with the following properties: tensile, 181 psi; elongation, 335 percent; and modulus at 100% elongation, 63 psi.

EXAMPLE 10

A two part formulation with fumed silica and calcium carbonate fillers was prepared, mixed and cured. A base was prepared by mixing 166.2 g calcium carbonate (Georgia Marble Corp. CS-11), 11.7 g silica (Cab-0-Sil LM-7), 93.9 g of polymer X, and 28.2 g of trimethylsiloxy terminated polydimethylsiloxane (100 cs viscosity) at high speed in a dental mixer for two minutes. a. Part A was formulated from 25 g of the base and 0.228 g of the hydrolyzate product of Example 4. Part B was formulated from 25 g of the base and 0.26 g diethylhydroxylamine. Parts A and B were co-extruded into a chase, tooled to form a slab and cured for 22 hrs at 50 percent relative humidity and 25° C. to give an elastomer with the following properties: tensile, 135 psi; elongation, 804 percent; and modulus at 100% elongation, 39 psi. b. Part A was formulated from Z5 g of the base and 0.57 g of the hydrolyzate product of Example 4 Part B was formulated from 25 g of the base and 0.26 g diethylhydroxylamine. Parts A and B were co-extruded into a chase, tooled to form a slab and cured for 22 hrs at 50 percent relative humidity and 25° C. to give an elastomer with the following properties: tensile, 91 psi; elongation, 646 percent; and modulus at 100% elongation, 33 psi.

That which is claimed is:

1. A polycyclosiloxane of the formula

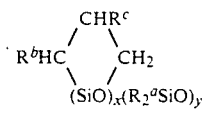

where $R^a$, $R^b$, amd $R^c$ are independently monovalent radicals selected from the group consisting of hydrogen atom, hydrocarbon, or substituted hydrocarbon; x is an integer equal to or greater than 3; y is equal to or greater than o, and x plys y is greater than 3.

2. The polycyclosiloxane of claim 1 wherein $R^b$ and $R^c$ are hydrogen, x is from 3 to 8 and y is zero.

3. The polycyclosiloxane of claim 1 wherein $R^b$ and $R^c$ are hydrogen, x is from 3 to 8 and y is greater than zero.

4. A process for the production of a polycyclosiloxane consisting essentially of
    (A) adding a solvent solution of 1,1-dichlorosilacyclobutane, and optionally dichlorodiorganosilane, to a mixture of water and solvent with rapid stirring at room temperature at a rate which does not cause the mixture to raise in temperature,
(B) washing with water,
(C) drying with dessicant,
(D) filtering, and
(E) removing the solvent, to yield

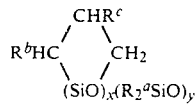

wherein $R^a$, $R^b$, and $R^c$ are independently monovalent radicals selected from the group consisting of hydrogen atom, hydrocarbon or substituted hydrocarbon; x is an integer equal to or greater than 3, y is equal to or greater than 0, and x plus y is greater than 3.

5. The process of claim 4 in which the solvent solution of (A) contains only 1,1-dichlorosilacyclobutane.

6. The process of claim 4 in which the dessicant is $MgSO_4$.

7. A silicone composition which cures on exposure to moisture to give an elastomer comprising
(A) 100 parts by weight of a silanol functional polydiorganosiloxane,
(B) from 0.1 to 100 parts by weight of the polycyclosiloxane of claim 1 in which y is zero, and
(C) from 0.01 to 1.0 part by weight of nucleophilic base.

8. The silicone composition of claim 7 in which the nucleophilic base in N,N-diethylhydroxylamine.

9. A silicone composition which cures to give an elastomer comprising
(A) 100 to 0 parts by weight of a silanol functional polydiorganosiloxane,
(B) 0.1 to 100 parts by weight of the polycyclosiloxane of claim 1 in which y is greater than zero, and
(C) from 0.01 to 1.0 parts by weight of nucleophilic base, part (C) being separated from the combination of part (A) and part (B) until the composition is to be used.

10. The silicon composition of claim 9 in which the nucleophilic base is N,N-diethylhydroxylamine.

11. The silicone composition of claim 9 in which (A) is 0.

12. A silicone composition which cures on exposure to moisture to give an elastomer comprising
(B) 100 parts by weight of the polycyclosiloxane of claim 1 in which y is greater than zero, and
(C) from 0.01 to 1.0 parts by weight of nucleophilic base.

13. The silicone composition of claim 12 in which the nucleophilic base is N,N-diethylhydroxylamine.

14. A silicone composition which is stored in two parts and which cures to give an elastomer upon mixing the two parts comprising
(A) 100 parts by weight of a silanol functional polydiorganosiloxane,
(B) 0.1 to 100 parts by weight of the polycyclosiloxane of claim 1 in which y is greater than zero, and
(C) from 0.01 to 1.0 parts by weight of nucleophilic base, part (C) being separated from the combination of part (A) and part (B) until the composition is to be used.

15. The composition of claim 14 in which the nucleophilic base is N,N-diethylhydroxylamine.

16. A silicone composition which is stored in two parts and which cures to give an elastomer upon mixing the two parts comprising
(A) 100 parts by weight of a silanol functional polydiorganosiloxane,
(B) 0.1 to 100 parts by weight of the polycyclosiloxane of claim 4 in which y is greater than zero, and
(C) from 0.01 to 1.0 parts by weight of nucleophilic base, one of the two parts being a portion of (A) and all of (B), and the other of the two parts being the remainder of (A) and all of (C).

17. The composition of claim 16 in which the nucleophilic base is N,N-diethylhydroxylamine.

* * * * *